(12) United States Patent
D'Amelio, Sr. et al.

(10) Patent No.: US 7,829,067 B2
(45) Date of Patent: Nov. 9, 2010

(54) METHOD AND COMPOSITION FOR TREATING ORAL BACTERIA AND INFLAMMATION

(75) Inventors: Frank S. D'Amelio, Sr., Huntington, NY (US); Youssef W. Mirhom, Huntington Station, NY (US)

(73) Assignee: Bio-Botanica, Inc., Hauppauge, NY (US)

( * ) Notice: Subject to any disclaimer, the term of this patent is extended or adjusted under 35 U.S.C. 154(b) by 86 days.

(21) Appl. No.: 10/791,290

(22) Filed: Mar. 3, 2004

(65) Prior Publication Data

US 2005/0196359 A1 Sep. 8, 2005

(51) Int. Cl.
*A61K 8/00* (2006.01)
*A61Q 11/00* (2006.01)
*A61K 8/02* (2006.01)

(52) U.S. Cl. ............... 424/49; 424/58; 424/401; 433/215; 433/216; 514/900; 514/902

(58) Field of Classification Search ............ 424/49, 424/58; 514/900
See application file for complete search history.

(56) References Cited

U.S. PATENT DOCUMENTS

| 5,145,665 | A | * | 9/1992 | Klueppel et al. | 424/50 |
|---|---|---|---|---|---|
| 5,472,684 | A | | 12/1995 | Nabi et al. | |
| 5,741,138 | A | * | 4/1998 | Rice et al. | 433/216 |
| 5,906,811 | A | | 5/1999 | Hersh | |
| 6,200,550 | B1 | * | 3/2001 | Masterson et al. | 424/49 |
| 6,228,347 | B1 | | 5/2001 | Hersh | |
| 6,231,836 | B1 | | 5/2001 | Takhtalian et al. | |
| 6,319,523 | B1 | | 11/2001 | Zhou | |
| 2001/0031744 | A1 | * | 10/2001 | Kosbab | 514/54 |
| 2002/0044977 | A1 | * | 4/2002 | Close | 424/725 |
| 2003/0198604 | A1 | * | 10/2003 | Lawlor | 424/49 |
| 2004/0039353 | A1 | * | 2/2004 | Koenig et al. | 604/289 |
| 2005/0158252 | A1 | * | 7/2005 | Romanowski et al. | 424/49 |

OTHER PUBLICATIONS

Harrison, Jim, Nature's Answer—For Your Health, p. 2, PerioCleanse, 2004.*
Harrison; "The Periodontal Solution: Healthy Gums Naturally"; Corinthian Health Press; 2001; pp. 95-107.

* cited by examiner

*Primary Examiner*—Frederick Krass
*Assistant Examiner*—Lezah W Roberts
(74) *Attorney, Agent, or Firm*—Roylance, Abrams, Berdo & Goodman, L.L.P.

(57) ABSTRACT

A composition and method for treating periodontal infections and gingivitis includes an extract of *Centipeda cunninghami*, coenzyme Q10, aloe vera and folic acid. The composition also contains additional plant extracts and nutrients that are effective in cell reproduction, wound healing and provide antibacterial and anti-inflammatory effects. The composition is applied to the teeth and gums to inhibit bacterial growth and reduce inflammation of the gums.

2 Claims, No Drawings

METHOD AND COMPOSITION FOR TREATING ORAL BACTERIA AND INFLAMMATION

FIELD OF THE INVENTION

The present invention is directed to a composition and method for treating the teeth and gums of a patient. In particular, the invention is directed to an oral composition for controlling infection of the gums and inflammation, inhibiting bacterial growth and encouraging healing of the gums.

BACKGROUND OF THE INVENTION

Periodontal disease is a prevalent health problem in adults. Gum disease is a form of periodontal disease which if not controlled or treated, can result in tooth loss. Gingivitis is the more common form of the various gum diseases that is caused by the bacteria on the teeth and gums. When the bacteria are not removed on a daily basis, the bacteria can build up. In the early stages, gingivitis can cause minor symptoms such as bad breath, bleeding and sensitivity of the gums. If not controlled, the bacteria that cause gingivitis can cause swelling and irritation of the gums and can lead to more severe forms of periodontal disease. The bacteria that cause the plaque build-up and gingivitis between the teeth and gums can cause infection of the gums if left untreated. The infection can cause eventually tooth damage and gum tissue damage. As the teeth loosen, additional build-up of the bacteria-infested plaque can occur.

Regular flossing and brushing of the teeth is generally recommended as a preventative for gum disease. Brushing and flossing of the teeth removes particles of food and the bacteria on the surfaces of the teeth that cause plaque. The daily oral hygiene can prevent or reduce the build-up of plaque and bacteria on the surfaces of the teeth, particularly below the gum line. Once the plaque builds-up and hardens, the plaque and the resulting calculus deposits cannot be removed by brushing or flossing. Typically, the calculus must then be removed by mechanical scraping by a dentist or oral hygienist.

Various compositions in the form of toothpaste and oral rinses have been proposed for many years to reduce the build-up of bacteria on the surfaces of the teeth. Many of these products, while effective, are not able to remove the calculus deposits once they have formed. At this point, inflammation and irritation of the gum is common.

A number of toothpaste and oral rinse compositions have been proposed that contain constituents for killing the bacteria in the mouth and reducing inflammation of the gums. One example is disclosed in U.S. Pat. No. 6,231,836 to Takhtalian et al. This composition contains folic acid, zinc, myrrh oil and clove oil to provide antibacterial and anti-inflammatory properties. U.S. Pat. No. 6,228,347 to Hersh discloses a composition for reducing the symptoms of gum disease where the composition contains glutathione and a source of selenium. Other compositions for treating gum disorders and inhibiting the growth of oral bacteria are disclosed in U.S. Pat. No. 6,319,523 to Zhou which describes the use of licorice extract, and U.S. Pat. No. 5,906,811 to Hersh which describes a composition including glutathione, ascorbic acid, selenium and an amino acid.

The prior compositions have generally been effective for the intended purpose. However, there is a continuing need in the health care field for an improved and effective composition for treating gum disorders.

SUMMARY OF THE INVENTION

The present invention is directed to a composition and method for inhibiting the growth of oral bacteria. The invention is also directed to a composition and method for treating and inhibiting gum disease by applying the composition to reduce inflammation and promote healing of inflamed gums and other oral tissue.

Accordingly, a primary feature of the invention is to provide a composition that can be applied to the tooth and gum surfaces that is effective in inhibiting the growth of oral bacteria and thereby inhibiting gum disease. In one preferred embodiment of the invention, the composition contains naturally occurring active components from plant materials or extracts obtained from the plant materials.

The composition contains a number of plant extracts and plant materials that are combined in a manner to provide a synergistic effect in reducing or inhibiting the growth of bacteria on the surfaces of the teeth. The composition is also effective in reducing inflammation of the gum tissue that can be caused by calculus deposits and the bacteria normally present in the oral cavity.

Another feature of the invention is to provide a composition for inhibiting the growth of bacteria and reducing inflammation of the gums where the composition contains at least one extract of a plant material from the *Centipeda* genus. In one embodiment, the extract is obtained from *Centipeda cunninghami*. The extract typically contains a mixture of water soluble and water insoluble components from the plant material.

The various features of the invention are basically attained by providing a composition for inhibiting the growth of oral bacteria where the composition includes an extract of the *Centipeda* genus, coenzyme Q10, aloe vera gel, folic acid and a pharmaceutically acceptable carrier. The composition can be in the form of a gel, paste or oral rinse. The various extracts of the plant materials are combined to form a bioactive agent. The bioactive agent is included in an amount effective to inhibit the growth of bacteria and to treat and reduce inflammation of the gums.

The various aspects of the invention are also attained by providing a composition for inhibiting the growth of oral bacteria and reducing inflammation of the gums where the composition includes a carrier and a bioactive agent. The bioactive agent contains an extract of *Centipeda cunninghami*, coenzyme Q10, aloe vera gel and folic acid.

The various features of the invention are also attained by providing a method for treating periodontal infections comprising topically applying a composition to a target site of an animal in need thereof in an effective amount to inhibit bacterial growth and reduce inflammation of the gum tissue caused by periodontal infection. The composition includes an effective amount of a bioactive agent comprising an extract of *Centipeda Cunninghami*, coenzyme Q10, aloe vera gel and folic acid.

The various advantages and features of the invention will become apparent from the following detailed description of the invention, which discloses various preferred embodiments of the invention.

DETAILED DESCRIPTION OF THE INVENTION

The present invention is directed to a composition and to a method for treating, inhibiting or preventing infection and inflammation of tissue. The invention is particularly directed to an oral composition and to a method of treating oral or mucosa tissue. The composition of the invention is effective in inhibiting the growth of bacteria in the oral cavity that can cause various periodontal infections.

The composition of the invention typically contains a carrier and an effective amount of a bioactive agent. In one preferred embodiment, the bioactive agent is included in an amount to be effective in treating, inhibiting or preventing infection by inhibiting the growth of bacteria and reducing inflammation of tissue in a target site. The composition of the invention is particularly effective in treating the gums of an animal, and particularly humans.

The composition of the invention is a dentifrice that can be in the form of a mouthwash or toothpaste. In other embodiments, the composition is in the form of a gel or paste that can be applied to the gum surfaces by a dentist or clinician. The composition is applied to a target site of the gums to treat and inhibit the development of gum disease and to inhibit bacterial growth that can cause gingivitis and periodontal infections. In one preferred embodiment of the invention, the bioactive agent comprises a mixture of natural constituents from various plant materials. The plant constituents can be the plant leaves or flower or extracts from the plant or portions thereof. The plant extracts can be in the form of oils, tinctures, dried powders, pastes, and the like, depending on the plant material and source of the active components within the plant.

The bioactive component of the composition preferably includes a mixture of herbal extracts and plant extracts as a source of natural components that promote wound repair and cell renewal and cell reproduction to treat periodontal infections effectively. The cell renewal and cell repairing properties of the composition assist the patient in healing, repairing and regenerating the gum tissue that is damaged or inflamed by the bacteria, the infection and/or calculus deposits on the teeth.

A primary component of the bioactive agent of the invention is at least one extract from the *Centipeda* genus. A preferred species of the genus is *Centipeda cunninghami*. The extract is preferably obtained from the leaves of the plant by a suitable liquid extraction process. In one embodiment, the extract is obtained as an aqueous tincture that is then dried to a powder or paste. The extract obtained by this process contains primarily a water soluble fraction from the plant.

In one preferred embodiment, the extract of the *Centipeda cunninghami* is obtained by extraction with one or more water and alcohol mixtures. The extract can be obtained from several extraction steps using different alcohol to water ratios and then combining the extraction solutions. Preferably, the resulting extraction is a holistic extract that contains a water soluble fraction and an alcohol soluble fraction from the plant material. The resulting mixture of the solutions is then evaporated to dryness to obtain a substantially dry powdered extract.

The composition of the invention is a mixture of plant extracts that are blended in proportions to provide antibacterial and anti-inflammatory properties. In one embodiment of the invention, the bioactive agent of the composition includes an extract of *Centipeda cunninghami*, coenzyme Q10 and folic acid. In another embodiment, the bioactive agent also contains an extract, fraction or gel of aloe vera. The extract of *Centipeda cunninghami* has been found to be effective in reducing inflammation, promoting cell renewal of gum tissue and to be effective in inhibiting the growth of bacteria that can cause gingivitis and periodontal infections. The *Centipeda cunninghami* extract is included in an amount effective to reduce inflammation, promote cell renewal and inhibit growth of bacteria. The extract is particularly effective when used in combination with the other components of the invention. Typically, the bioactive agent contains about 5 wt % to about 30 wt %, and preferably about 9.0 wt % to about 11.0 wt % based on the weight of the bioactive agent.

Folic acid is effective in promoting cell reproduction and in reducing gum inflammation and bleeding. The folic acid is included in the bioactive agent in an amount of about 0.5 wt % to about 1.0 wt %, and preferably about 0.9 wt % to about 1.1 wt % based on the total weight of the bioactive agent. Coenzyme Q10 is typically included in amounts of about 0.1 to 0.4 wt %, and preferably about 0.2 wt % based on the total weight of the bioactive agent.

The amount of the *Centipeda cunninghami* extract, coenzyme Q10 and folic acid depend in part on the number of components that are used to make up the bioactive agent. In one embodiment, these three components are used in substantially equal amounts by weight. The amounts of these components can be more or less than the percentage noted above to make up the bioactive agent.

The bioactive agent preferably contains an extract of *Centipeda cunninghami*, folic acid and coenzyme Q10 as essential components. In one preferred embodiment, the composition also contains at least one component or extract selected from the group consisting of aloe vera, prickly ash bark, Echinacea, gotu kola extract, chamomile extract, olive leaf extract, black walnut hulls extract, grapefruit seed extract, green tea extract containing about 50 wt % polyphenols, chlorophyll KK, peppermint oil, oregano oil, lavender oil, clove bud oil, thyme oil, eucalyptus oil, cinnamon bark oil, bio-saponin concentrate, and mixtures thereof. Each of these components can be combined in various amounts to provide the desired antibacterial and anti-inflammatory properties of the final composition. Typically, these components are included in amounts of about 1.0 wt % to about 10 wt % based on the total weight of the bioactive agent. In other embodiments, the bioactive agent can contain about 2-10 wt % Vitamin E.

The bioactive agent can be prepared initially as a concentrate that is later mixed with a suitable carrier in therapeutically effective amounts. When the bioactive agent is prepared as a concentrate, the bioactive agent is mixed with a carrier to produce the final composition typically containing about 5.0 wt % to about 25 wt % of the bioactive agent and about 75 wt % to about 95 wt % of a carrier and other components such as humectants, emollients, stabilizers, surfactants, emulsifying agents and flavoring agents. In preferred embodiments, the composition comprises about 10 wt % to about 15 wt % of the bioactive agent with the balance being a carrier and other components.

In one embodiment of the invention, the composition contains about 5.0 wt % to about 15 wt % of the bioactive agent where the bioactive agent contains a mixture of *Centipeda cunninghami* extract, aloe vera gel, coenzyme Q10, folic acid, and at least one additional plant extract identified above. In this embodiment, the bioactive agent contains *Centipeda cunninghami* extract in an amount of about 10 wt % to about 35 wt % based on the total weight of the bioactive agent. The bioactive agent in one embodiment includes about 10 wt % to 35 wt % coenzyme Q10, about 10 wt % to 35 wt % folic acid, and about 10 wt % to 35 wt % aloe vera gel.

In one embodiment of the invention, the composition includes the bioactive agent dispersed in a carrier in an amount to obtain a final composition containing about 0.5 wt % to about 1.5 wt % Aloe vera Phytogel
    about 0.05 wt % to about 0.2 wt % Folic Acid
    about 0.25 wt % to about 0.75 wt % NE, Prickly Ash Bark Extract
    about 1.0 wt % to about 1.5 wt % NE, Calendula Extract (Marigold)

about 0.75 wt % to about 1.5 wt % NE, Echinacea purp. Tops
about 0.25 wt % to about 0.75 wt % NE, Gotu Kola Extract
about 0.75 wt % to about 1.5 wt % NE, Chamomile Extract
about 0.5 wt % to about 1.0 wt % *Centipeda cunninghami* Extract
about 0.05 wt % to about 0.1 wt % NE, Olive Leaf Extract
about 0.02 wt % to about 0.1 wt % NE, Black Walnut Hulls Extract
about 0.03 wt % to about 0.1 wt % NE, Grape Fruit Seed Extract
about 0.01 wt % to about 1.0 wt % Green Tea, PE 50% Polyphenols less than 0.1 wt % Chlorophyll KK
about 1.5 wt % to about 2.5 wt % Peppermint Oil
about 0.2 wt % to about 1.0 wt % Oregano Oil
about 0.1 wt % to about 0.5 wt % Lavender Oil
about 0.1 wt % to about 0.5 wt % Clove Bud Oil
about 0.05 wt % to about 0.1 wt % Thyme Oil
about 0.05 wt % to about 0.1 wt % Eucalyptus Oil
about 0.02 wt % to about 0.1 wt % Cinnamon Bark Oil
about 0.5 wt % to about 1.5 wt % Bio-Saponin Conc.
about 0.02 wt % to about 0.1 wt % Coenzyme Q10 and the balance being a carrier.

In one embodiment of the invention, the carrier is glycerin or an aqueous-glycerin mixture. In other embodiments, the carrier can be a standard liquid, gel, solid or semi-solid carrier composition that is suitable for oral use. The resulting composition can be used by applying directly to the target site to inhibit the growth of bacteria and reduce inflammation of the gum tissue caused by the periodontal infection.

The oral compositions of the invention are prepared as a mixture of a bioactive agent and a suitable carrier. The carrier is a liquid, gel or paste that is pharmaceutically acceptable to be applied directly to the surfaces of the teeth and gums. The bioactive agent is combined with the carrier in a therapeutic amount effective to treat the surface in the oral cavity. Typically, the bioactive agent is combined with the carrier in an amount of about 5.0 wt % to about 15 wt % based on the total weight of the oral composition.

As used herein, the bioactive agent refers to the mixture of the various active plant materials and extracts in a concentrated form compared to the concentration in the original plant material. The bioactive agent is typically a mixture of the materials without a solvent, carrier or vehicle. In other embodiments, the bioactive agent can contain small amounts of a carrier or vehicle to enable sufficient mixing, handling and dispensing of the components in the final composition.

Each of the components of the composition have been found to have a particular effect in treating periodontal infections. The combination of the components has also been found to have a synergistic effect that inhibit the growth of bacteria in the mouth. The combination of the components also provide a synergistic effect in promoting cell renewal of the gum tissue and reducing inflammation. Aloe vera gel as used in the present invention is included in an amount to provide an anti-inflammatory effect caused by the periodontal infection. In addition, the aloe vera gel is provided in an amount to prevent the inflammation that can sometimes be caused by some of the other components of the composition. Folic acid is a B vitamin and is included in an amount to promote cell renewal. Folic acid is also a free radical scavenger that can be effective in reducing inflammation.

The calendula extracts have been found to have in vitro antibacterial, anti-fungal, and astringent properties. The calendula extracts are also effective in promoting healing and reducing inflammation. The echinacea purpurea plant and the extracts from the plant are included as antibacterial and cell renewing agent. The gotu kola is included in amounts to stimulate wound healing. The triterpenoids of the extract by promoting collagen production and having anti-inflammatory properties. The chlorophyll is included in amounts to reduce odors and to promote healing of the wounds. The extract of the *Centipeda cunninghami* is included in an amount to provide anti-inflammatory and cell renewing properties. The prickly ash bark extract is used in an amount as a pain reliever and as an anti-inflammatory agent. The green tea is included to inhibit the growth of bacteria that can cause tooth decay. The oregano oil contains primarily carvacrol and thymol that have antiseptic properties sufficient to kill bacteria and various microorganisms. The peppermint oil is included in an amount to provide an antiviral activity. Peppermint oil also contains Azulene, which exhibits anti-inflammatory and anti-ulcerogenic effects. Chamomile oil is an effective antibacterial and deodorant with anti-inflammatory properties. The chamomile oil also promotes granulation and epithelization. Clove oil contains Eugenol having antiseptic and anesthetic properties. Cinnamon oil is included in an amount to provide antibacterial and anti-fungal properties. Eucalyptus oil is included as an antiseptic with deodorant and providing a cooling sensation to the gums.

Oil of lavender is included as an antiseptic, a deodorant and as a fragrance. Thyme oil is included as an antiseptic and antibacterial agent against many microorganisms. Thyme oil is also effective in reducing inflammation. Bio-saponins are included as surfactants to promote the miscibility of water insoluble components and to enhance the penetration of the composition to the spaces between the teeth and to effectively attack the microorganisms being treated. Coenzyme Q10 is included in an amount to promote repair and maintenance of periodontal tissue.

The extract from the *Centipeda cunninghami* can be obtained by various methods. In preferred embodiments, the resulting extract is a holistic mixture of active components in substantially the same ratio as the active components that are present in the native plant material. The extract is obtained by grinding, cutting or pulverizing the plant material and contacting in a suitable extracting solvent. The resulting mixture is then filtered to separate the solid particles. The volume of the extraction liquid is then reduced. Typically, the resulting extract is dried to produce a dry powder.

The extraction process for the *Centipeda cunninghami* is obtained using a suitable solvent which can be a polar, non-polar, semi-polar solvent and mixtures thereof. Suitable polar solvents include lower alkyl alcohols and lower alkyl ethers. Other solvents include lower alkyl ketones and aldehydes. In one embodiment, the extraction process uses a series of aqueous ethanol mixtures containing different amounts of ethanol. Each of the extraction solvent mixtures are used to extract the plant material and the resulting extracts combined to form a single extract. Examples of suitable extraction processes and the resulting extract are disclosed in the commonly owned U.S. Pat. No. 5,804,206 to D'Amelio et al., which is hereby incorporated by reference in its entirety.

The bioactive agent of the invention can be dispersed in any suitable vehicle or carrier. In one embodiment, the carrier is glycerin which can then be dispersed in water to obtain the desired concentration. In other embodiments, the carrier can be an aqueous system containing suitable emulsifiers, surfactants or cosolvents suitable for dissolving or dispersing the various components within the system. The carriers can be in the form of gels or toothpaste suitable for applying the composition directly to the gums.

In one embodiment, the composition is prepared as a gel or paste containing bicarbonates and various thickening agents. Various thickeners can include various vegetable gums such as chicle, xanthan, arabic, karaya and tragacanth. Various alginates, carageenans and cellulose derivatives, such as sodium carboxymethyl, methyl and hydroxy ethyl derivatives can be used. Various non-nutritive sweeteners or other natural sweeteners such as Xylitol can be used. Sorbitol is also a suitable sweetener that can be used in the composition, if desired.

Oral gels and toothpastes can also include other antiplaque components, other antimicrobial agents to inhibit bacteria reproduction and fluorides. Examples of suitable fluoride components include sodium fluoride, stannous fluoride and sodium monofluorophosphate. Typically, a suitable polishing agent is included in the gel or paste vehicle to form the dentifrice. Examples of polishing agents include dibasic calcium phosphate, tribasic calcium phosphate, aluminum hydroxide, magnesium carbonate, calcium carbonate, calcium pyrophosphate, calcium sulfate, bentonite, alumina, hydrated alumina, aluminum silicate, zirconium silicate, silica, and mixtures thereof.

The resulting composition of the invention when in the form of a gel or paste is used in a manner similar to conventional toothpastes. The gel or paste containing the bioactive agent is applied while brushing to contact the teeth and gums, followed by rinsing.

In other embodiments, the composition is an oral rinse such as a mouthwash that contains about 60-90% by weight of a liquid carrier. The carrier is typically an aqueous mixture that can contain or more cosolvents, surfactants or dispersing agents. In one embodiment, the oral rinse can contain about 5-30% by weight of a non-toxic alcohol such as ethanol. The oral rinse is used in a conventional manner by contacting the teeth and gums with the rinse for about one minute. In further embodiments, the composition can be used in the form of a lozenge or chewing gum.

In further embodiments of the invention, the composition is in the form of a gel, paste or liquid that can be applied directly to the gums or other oral tissue where the composition remains in contact with the target tissue for extended periods of time. The composition can, for example, be in the form of a gel that is injected or otherwise introduced under the gums between the teeth and gums of the patient to treat the infected site. The gel is allowed to remain to provide complete and effective treatment of the infected and inflamed gums.

The following is a non-limiting example of one embodiment of the composition.

EXAMPLE

In this example, an oral preparation was produced from a mixture of plant extracts for treating the gums of a patient exhibiting inflammation and swelling of the gums caused by periodontal infections. In this example, 0.417 Kg of prickly ash bark extract, 1.667 Kg of calendula extract, 1.267 Kg of echinacea, 0.627 Kg of gotu kola extract, 1.267 Kg of chamomile extract, 0.862 Kg of *Centipeda cunninghami* extract, 0.832 Kg of olive leaf extract, 0.033 Kg of black walnut hull extract and 0.042 Kg of grapefruit seed extract were added to 10 Kg glycerin. The resulting mixture was autoclaved to sterilize the components.

In a separate container, a paste was prepared from 1 Kg of aloe vera, 0.167 Kg folic acid, 0.032 Kg coenzyme Q10 in 1 Kg of bio-saponin concentrate and the resulting paste was mixed well in 10 Kg of glycerin. This mixture was then added slowly with continuous stirring to another container that contained 70 kg glycerin. The mixture was continuously mixed to prevent the solids from settling at the bottom. The resulting mixture was warmed to completely dissolve or disperse the components and homogenized by mixing. To this mixture, 0.20 Kg of green tea extract and 833 mg of chlorophyll KK were added sequentially and warmed to dissolve. The resulting second mixture was then added to the first mixture slowly with continuous mixing and cooling slowly. After cooling, the volatile oils were sequentially added and mixed. The oils that were added included 2.7 Kg peppermint oil, 0.379 Kg oregano oil, 0.223 Kg lavender oil, 0.175 Kg clove bud oil, 0.076 Kg thyme oil, 0.076 Kg eucalyptus oil, and 0.044 Kg cinnamon bark oil. After mixing completely, 21.98 Kg of glycerin was then added and mixed well. The resulting composition is shown in Table I where the percentages are by weight based on the total weight of the composition.

TABLE I

| AMOUNT | % w/w | INGREDIENT |
| --- | --- | --- |
| 1.002 Kg | 0.800% | Aloe vera Phytogel |
| 0.167 Kg | 0.134% | Folic Acid |
| 0.417 Kg | 0.330% | NE, Prickly Ash Bark |
| 1.667 Kg | 1.338% | NE, Calendula (Marigold) |
| 1.267 Kg | 1.017% | NE, Echinacea purp. Tops |
| 0.627 Kg | 0.504% | NE, Gotu Kola |
| 1.267 Kg | 1.017% | NE, Chamomile |
| 0.862 Kg | 0.692% | *Centipeda cunninghami* Extract in BG |
| 0.0832 Kg | 0.067% | NE, Olive Leaf |
| 0.033 Kg | 0.026% | NE, Black Walnut Hulls |
| 0.042 Kg | 0.034% | NE, Grapefruit Seed |
| 0.020 Kg | 0.016% | Green Tea, PE 50% Polyphenols |
| 833 mg* | 0.000669% | Chlorophyll KK |
| 2.700 Kg | 2.168% | Peppermint Oil |
| 0.379 Kg | 0.304% | Oregano Oil |
| 0.223 Kg | 0.179% | Lavender Oil |
| 0.175 Kg | 0.140% | Clove Bud Oil |
| 0.076 Kg | 0.061% | Thyme Oil |
| 0.076 Kg | 0.061% | Eucalyptus Oil |
| 0.044 Kg | 0.035% | Cinnamon Bark Oil |
| 1.000 Kg | 0.803% | Bio-Saponin Conc. |
| 0.032 Kg | 0.026% | Coenzyme Q10 |
| 111.98 Kg | 89.879% | Glycerin |
| Total 124.5 Kg | 100% | |

NE = Native Extract

The resulting composition is applied to the areas of inflammation of the gums to reduce the inflammation, inhibit the growth of oral bacteria and promote healing.

While various embodiments of the invention have been described herein, it will be understood by those skilled in the art that various changes and modifications can be made without departing from the scope of the invention as defined in the appended claims.

What is claimed is:

1. An oral composition for inhibiting the growth of oral bacteria, wherein said composition includes an effective amount of a bioactive agent which comprises:
    about 0.5 wt % to about 1.5 wt % aloe vera extract;
    about 0.05 wt % to about 0.2 wt % folic acid;
    about 0.25 wt % to about 0.75 wt % prickly ash bark extract;
    about 1.0 wt % to about 1.5 wt % calendula extract;
    about 0.75 wt % to about 1.5 wt % echinacea extract;
    about 0.25 wt % to about 0.75 wt % gota kola extract;

about 0.75 wt % to about 1.5 wt % chamomile extract;
about 0.5 wt % to about 1.0 wt % *Centipeda cunninghami* extract;
about 0.05 wt % to about 0.1 wt % olive leaf extract;
about 0.02 wt % to about 0.1 wt % black walnut hull extract;
about 0.03 wt % to about 0.1 wt % grape fruit seed extract;
about 0.01 wt % to about 1.0 wt % green tea extract;
less than 0.1 wt % chlorophyll;
about 1.5 wt % to about 2.5 wt % peppermint oil;
about 0.2 wt % to about 1.0 wt % oregano oil;
about 0.1 wt % to about 0.5 wt % lavender oil;
about 0.1 wt % to about 0.5 wt % clove bud oil;
about 0.05 wt % to about 0.1 wt % thyme oil;
about 0.05 wt % to about 0.1 wt % eucalyptus oil;
about 0.02 wt % to about 0.1 wt % cinnamon bark oil;
about 0.5 wt % to about 1.5 wt % bio-saponin; and
about 0.02 wt % to about 0.1 wt % coenzyme Q10;
wherein said percentages are based on the weight of the composition.

2. A method of treating periodontal infection and inhibiting growth of oral bacteria and treating inflammation by applying a composition to a target site, wherein said composition comprises:
about 0.5 wt % to about 1.5 wt % aloe vera extract;
about 0.05 wt % to about 0.2 wt % folic acid;
about 0.25 wt % to about 0.75 wt % prickly ash bark extract;
about 1.0 wt % to about 1.5 wt % calendula extract;
about 0.75 wt % to about 1.5 wt % echinacea extract;
about 0.25 wt % to about 0.75 wt % gota kola extract;
about 0.75 wt % to about 1.5 wt % chamomile extract;
about 0.5 wt % to about 1.0 wt % *Centipeda cunninghami* extract;
about 0.05 wt % to about 0.1 wt % olive leaf extract;
about 0.02 wt % to about 0.1 wt % black walnut hull extract;
about 0.03 wt % to about 0.1 wt % grape fruit seed extract;
about 0.01 wt % to about 1.0 wt % green tea extract;
less than 0.1 wt % chlorophyll;
about 1.5 wt % to about 2.5 wt % peppermint oil;
about 0.2 wt % to about 1.0 wt % oregano oil;
about 0.1 wt % to about 0.5 wt % lavender oil;
about 0.1 wt % to about 0.5 wt % clove bud oil;
about 0.05 wt % to about 0.1 wt % thyme oil;
about 0.05 wt % to about 0.1 wt % eucalyptus oil;
about 0.02 wt % to about 0.1 wt % cinnamon bark oil;
about 0.5 wt % to about 1.5 wt % bio-saponin; and
about 0.02 wt % to about 0.1 wt % coenzyme Q10,
wherein each of said extracts is included in an effective amount to treat inflammation and inhibit growth of oral bacteria and where the percentages are based on the weight of the composition.

* * * * *